(12) United States Patent
Wright et al.

(10) Patent No.: US 9,266,798 B1
(45) Date of Patent: Feb. 23, 2016

(54) ACYCLIC MONOTERPENES AS BIOFUELS BASED ON LINALOOL AND METHOD FOR MAKING THE SAME

(71) Applicant: THE UNITED STATES OF AMERICA AS REPRESENTED BY THE SECRETARY OF THE NAVY, Washington, DC (US)

(72) Inventors: Michael E. Wright, Ridgecrest, CA (US); Roxanne L. Quintana, Ridgecrest, CA (US); Benjamin G. Harvey, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/494,287

(22) Filed: Sep. 23, 2014

Related U.S. Application Data

(60) Division of application No. 13/608,749, filed on Sep. 10, 2012, now Pat. No. 8,987,539, which is a continuation-in-part of application No. 12/550,973, filed on Aug. 31, 2009, now Pat. No. 8,227,651, and a continuation-in-part of application No. 12/511,796, filed on Jul. 29, 2009, now Pat. No. 8,395,007.

(60) Provisional application No. 61/532,462, filed on Sep. 8, 2011.

(51) Int. Cl.
| | |
|---|---|
| *C07C 1/20* | (2006.01) |
| *C07C 9/16* | (2006.01) |
| *C07C 1/24* | (2006.01) |
| *C10L 1/04* | (2006.01) |
| *C10M 105/04* | (2006.01) |
| *C07C 5/03* | (2006.01) |
| *C07C 1/00* | (2006.01) |
| *C07C 1/207* | (2006.01) |
| *C07C 9/14* | (2006.01) |
| *C07C 9/22* | (2006.01) |
| *C07C 2/00* | (2006.01) |

(52) U.S. Cl.
CPC ... *C07C 9/16* (2013.01); *C07C 1/20* (2013.01); *C07C 1/24* (2013.01); *C07C 5/03* (2013.01); *C10L 1/04* (2013.01); *C10M 105/04* (2013.01); *C07C 2523/44* (2013.01)

(58) Field of Classification Search
CPC ............ C07C 1/00; C07C 1/20; C07C 1/207; C07C 2/00; C07C 2/04; C07C 2/74; C07C 9/14; C07C 9/16; C07C 9/22
See application file for complete search history.

(56) References Cited

U.S. PATENT DOCUMENTS

| | | | |
|---|---|---|---|
| 7,540,888 B2 | 6/2009 | Ryder et al. | |
| 7,589,243 B1 | 9/2009 | Ryder | |
| 2003/0051988 A1* | 3/2003 | Gunnerman et al. | .... 204/157.15 |

OTHER PUBLICATIONS

Won, S.H. et al. (2014). Combustion and Flame, 161, 826-834.*
Van Looveren, et al. Methylalumoxane MCM-41 as support in the co-oligomerization of ethene and propene with {C2H4(1-indenyl)2}Zr(CH3)2], Angew. Chem. Ed. 1998, 37, No. 4.
Madhavan, et al., Dimerisation of olefins catalysed by K10-montmorillonite clays, Catalysis Letters vol. 73, No. 1, 2001.

* cited by examiner

*Primary Examiner* — Brian McCaig
(74) *Attorney, Agent, or Firm* — Charlene A. Haley (57) ABSTRACT

Acyclic monterpene alcohols, like linalool, to be converted through a series of highly efficient catalytic reactions a bio-gasoline blending component, and a drop-in biodiesel fuel.

7 Claims, 9 Drawing Sheets

ACYCLIC MONOTERPENES AS BIOFUELS BASED ON LINALOOL AND METHOD FOR MAKING THE SAME

CROSS-REFERENCE TO RELATED APPLICATIONS

This is a divisional application, claiming the benefit of, parent application Ser. No. 13/608,749 filed on Sep. 10, 2012 which is now U.S. Pat. No. 8,987,539 filed on Sep. 10, 2012, which is the non-provisional parent application Ser. No. 61/532,462 filed on Sep. 8, 2011 and continuation-in-part application claiming benefit of parent application Ser. No. 12/550,973 filed on Aug. 31, 2009, which is now U.S. Pat. No. 8,227,651 and Ser. No. 12/511,796 filed on Jul. 29, 2009, which is now U.S. Pat. No. 8,395,007, whereby the entire disclosures of which are incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to a method including acyclic monterpene alcohols, like linalool, to be converted through a series of highly efficient catalytic reactions a biogasoline blending component and a drop-in biodiesel fuel.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to a method including acyclic monterpene alcohols, like linalool, to be converted through a series of highly efficient catalytic reactions a biogasoline blending component, and a drop-in biodiesel fuel.

Embodiments of the invention generally relate to methods for manufacturing fuels and lubricant additives including, hydrogenating at least one acyclic monoterpene alcohol with at least one transition metal hydrogenation catalyst to produce a fully saturated monoterpene alcohol tetrahydrolinalool (THL), dehydrating the tetrahydrolinalool (THL) with at least one acid catalyst and azeotropic distillation and recovering benzene to produce 3,7-dimethyloctene isomers, acid catalyzing reaction of the 3,7-dimethyloctene isomers and recovering benzene, hydrogenating the 3,7-dimethyloctene isomers with at least one transition metal catalyst to produce a mixture of 2,6-dimethyloctane (DMO), dimers ($C_{20}$ isomers), and trimers ($C_{30}$ isomers), distillation isolating the 2,6-dimethyloctane (DMO), dimers ($C_{20}$ isomers), and trimers ($C_{30}$ isomers) from the mixture to produce a substantially purified set of $C_{10}$ to $C_{30}$ for produce the fuels, and leaving the distillation pot residue ($C_{40}$+) for subsequent use biolubricant additives.

Other embodiments of the invention generally relate to methods for manufacturing fuels including, hydrogenating at least one acyclic monoterpene alcohol (linalool) with at least one catalyst included of a late transition metal to produce tetrahydrolinalool (THL), dehydrating the tetrahydrolinalool (THL) with at least one acid catalyst and azeotropic distillation and recovering benzene to produce 3,7-dimethyloctene isomers, and hydrogenating the 3,7-dimethyloctene isomers with at least one late transition metal catalyst to produce 2,6-dimethyloctane (DMO).

In embodiments, at least acyclic monoterpene alcohol is linalool or perillyl alcohol. In embodiments, the transition metal catalyst is palladium supported on carbon. In embodiments, at least one acid catalyst selected from the group consisting of montmorillonite K10, sulfonated polystyrene to include Amberlyst-15 and Amberlyst-35, sulfonated poly-p-phenylenes, sulfonated silica materials, and similar solid supports bearing a sulfonic acid moiety. In embodiments, the thermal dimerizing method includes increasing the temperature to accelerate the dimerization of the 3,7-dimethyloctene isomers to produce 2,6-dimethyloctane (DMO), dimers ($C_{20}$ isomers), and trimers ($C_{30}$ isomers). In embodiments, at least one hydrgenation catalyst is selected from the group consisting of palladium on carbon, palladium hydroxide on carbon, platinum oxide, platinum on carbon, nickel/aluminum alloy, and any combination thereof.

In embodiments, the fuel is 2,6-dimethyloctane (DMO). The embodiments further include recombining portions of DMO, C-20 dimer, and C-30 trimer that meet ASTM D975 specifications for Diesel #2. In other embodiments, at least transition metal hydrogenation catalyst is palladium on carbon, palladium hydroxide on carbon, platinum oxide, platinum on carbon, nickel/aluminum alloy, and any combination thereof. Embodiments further include combining a mixture of $C_{20}$ dimer, $C_{30}$ trimer, and pot residue ($C_{40}+$) to meet DAE standard for specific weights of lubricant oils. Embodiments further include combining 2,6-dimeethyloctane (DMO), a fully saturated C15 sesquiterpene (farnesane), and dimers (C20 isomers) that meets ASTM specifications D975.

Another aspect of the invention generally relates to fuels produced by the methods therein. Other aspects of the invention generally relate to fuel blends produced by combining 2,6-dimethyloctane (DMO) and dimers ($C_{20}$ isomers) which are produced by the methods herein. Yet other aspects of the invention include lubricants and/or additives produced by the methods herein. Still yet other aspects of the invention include fuel blends produced by the methods herein.

Furthermore, a catalytic system was developed that can effectively dehydrate tetrahydrolinalool and then sequentially convert the product of dehydration into a series of biolubricants or heavy diesel fuel (equivalent or superior to F-76 ship fuel) with excellent cold flow properties, no aromatics, and no sulfur. By suspending the catalyst and exposing only the vapors of the reaction mixture to catalyst very selective dimerization occurs without deactivation of the catalyst.

Biofuel and Biolubricants derived from Linalool and related monoterpene alcohols address carbon dioxide emission issues (zero net green house gas emissions), have no sulfur content, reduce particulate emissions, and lower NOx emissions in both diesel and turbine applications. They are completely renewable and greatly alleviate the need (i.e. dependence upon) on petroleum based fuels and lubricants. Developed here is a method for creating diesel, jet, and ship fuels/lubricants from monoterpene alcohols. They provide excellent low temperature performance, high fuel energy content, and represents fully sustainable and renewable (100% independent from petroleum products and processes) based on a feedstock of monoterpene alcohols.

Department of Defense has significant interest in alternative biofuels for securing national security. Linalool has not been successfully converted to a diesel or jet/diesel fuel nor lubricants in prior art. The ability to convert linalool and related monoterpene alcohols in about 100% chemical efficiency to drop-in diesel fuels and a major component of a surrogate jet fuel is a breakthrough. In addition, by creating chemistries to build dimers, trimers, and/or tetramers of the monoterpene alcohol carbon skeleton can create biolubricants with tailored viscosities directly from a monoterpene alcohol.

There exists a great need for the development of multiple and varied routes to biofuels and biolubricants. The biosynthesis of monoterpene alcohols is widespread in nature. However, little work has been done to show their utility in creating new biogasoline, biodiesel and biojet fuels, and biolubricants. This invention describes a method for rapidly and effectively converting a monoterpene alcohol into a useful array of fuels and lubricants by applying a unique set of reaction conditions and strategies. In addition, by using $C_{20}$ (dimers of the monoterpene) as part of the jet fuel blend, a very positive effect can be induced for lubricity.

Previous work and patents by Amyris have addressed the biosynthesis of a sesquiterpene (farnesene) and utility in the areas of diesel fuel, jet fuel, and biolubricants. The monoterpene used in their surrogate jet fuel was based on cyclic monoterpene limonene, the later has little value as a diesel fuels (low Cetane index). They also never disclose any chemistry for converting the cyclic monoterpene to larger (i.e. dimer, trimer . . . ) molecules capable of having value as a biolubricant. Farnesene was copolymerized with ethylene gas to form biolubricants using certain transition metal catalysts (U.S. Pat. No. 7,589,243).

No previous work has described the use of monoterpene alcohols to prepare gasoline, diesel and/or jet fuels. The conversion of monoterpene alcohols to biolubricants is also an unknown art. This work brings to light a significant breakthrough in the area of utilizing and preparing new gasoline blends, biodiesel, surrogate jet fuels blends, and biolubricants all based on a simple and readily available monoterpene alcohol biofeedstock via a unique chemical approach.

Acyclic monterpene alcohols, like linalool, can be converted through a series of highly efficient catalytic reactions to a biogasoline blending component and a drop-in biodiesel fuel. Furthermore, a catalytic system was developed that can effectively dehydrate tetrahydrolinalool and then sequentially convert the product of dehydration into a series of biolubricants or heavy diesel fuel (equivalent or superior to NAVY F-76 ship fuel) with adequate cold flow properties, no aromatics, and no sulfur. Thus, a pure synthetic paraffinic kerosene fuel is created as part of this instant invention. By suspending the catalyst and exposing only the vapors of the reaction mixture to catalyst very selective dimerization occurs without deactivation of the catalyst. Other embodiments include condensing the vapors on the solid acid catalyst and then flashing the unreacted monoterpene for recycle back to the catalyst. In this latter process, not only is the catalyst lifetime extended but also formation of the trimer ($C_{30}$) products can be controlled.

Terpenes represent the most ubiquitous and varied organic structures in the World of biosynthesized molecules. The role they play in terms of structural and biological activity are equally numerous and diverse. In terms of generating biofuels they have the attractive feature of being pure hydrocarbons with often little unsaturation. Thus, conversion to a fully saturated hydrocarbon fuel with combustion performance equal to or exceeding typical gasoline/diesel/jet fuels is possible with little chemical processing required. There are examples where trees can "deliver" terpene-based fuels that can be used directly in diesel engines. Recently demonstrated, was that β-pinene can be dimerized, then hydrogenated, to form high-density turbine fuel (i.e. JP-10) candidate. Amyris has eloquently shown that farnesene can be biosynthesized and over-expressed in yeast at an industrial scale to produce a sesquiterpene ($C_{15}$) hydrocarbon that after hydrogenation, can be used as a drop-in diesel fuel and as a minor component of a surrogate jet fuel blend.

Acyclic monoterpenes ($C_{10}$ hydrocarbons) are also key candidates for the creation of diesel and jet fuels having a flash point near or above 38° C. A very attractive feature of several acyclic monoterpenes is that they can be readily converted to bio-alkylaromatics through high yielding thermally induced rearrangements. The bio-alkylaromatics can serve a role in swelling legacy rubber seals (e.g. jet fuels) and increasing/modifying the octane rating for gasoline applications. In addition, the bio-alkylaromatics can be used to make monomers for polymers and composites. Thus acyclic monoterpenes can play a host of roles in preparing several classes of chemical bio-products. This invention continues with a Naval Air Warfare Center Weapons Division (NAWCWD) theme for developing gasoline, diesel, and jet fuels based on discrete and well defined bio-platform molecules followed by well defined chemical reactions that can then provide a variety of biofuel candidates.

Initially the program began to investigate both linalool and geraniol as possible monoterpene feedstocks. Interestingly, it was discovered that geraniol is much more difficult to hydrogenate under typical reaction conditions (e.g. palladium catalyst, 50 psig hydrogen, ambient temperature) known to those experienced in the art of hydrogenation ("X" shows that the reaction does not work well). Although, not explainable at this time, it appears as though the geraniol is capable of deactivating the hydrogenation catalyst and it was discovered that geraniol is much more aggressive in attacking rubber seals/stoppers found on the hydrogenation apparatus.

Figure 9:
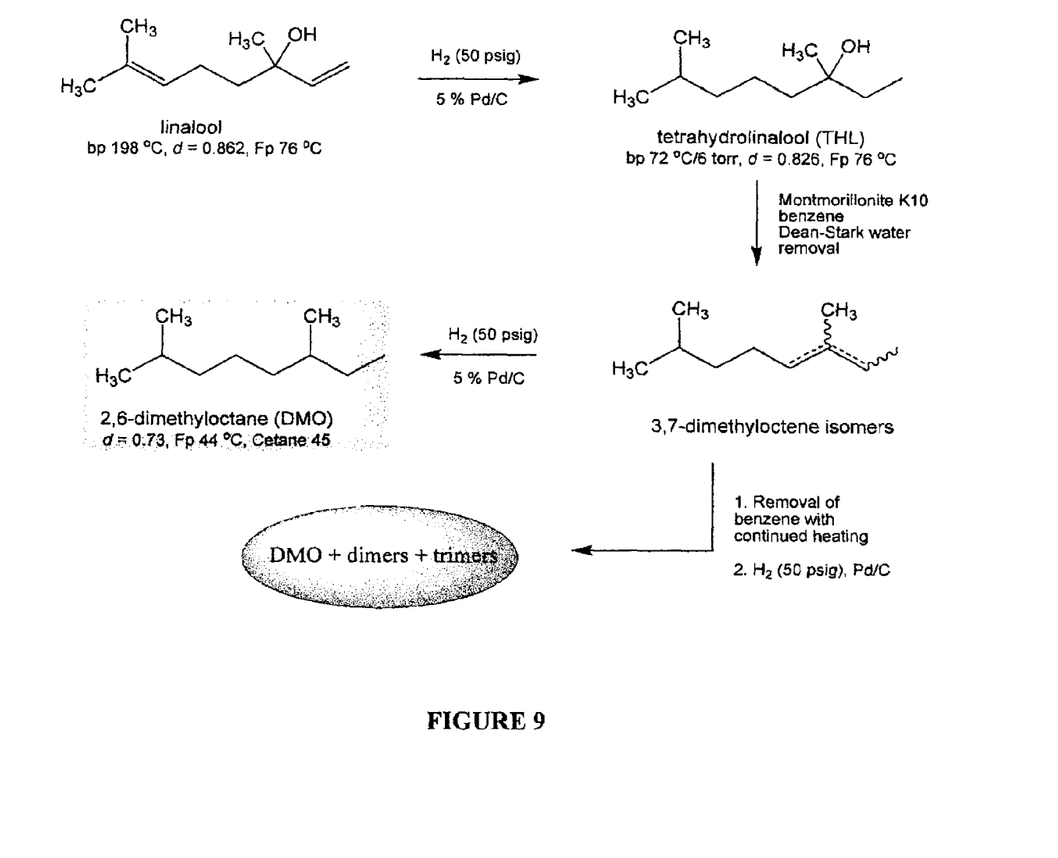
FIG. 9 is a chemical schematic showing linalool nicely undergoing hydrogenation using mild conditions to afford tetrahydrolinalool (THL) in near auantitarive conversions, according to embodiments of the invention.

On the other hand, it was discovered that linalool very nicely undergoes hydrogenation using mild conditions to afford tetrahydrolinalool (THL) in near quantitative conversions as shown in FIG. 9.

THL purchased from Aldrich Chemical and that prepared in our hands by the dehydration/reduction of linalool with no detectable differences in quality and/or behavior.

Montmorillonite K10 Dehydration/Oligomerization. In using the clay montmorillonite K10 as the acid catalyst for dehydration of THL it was discovered that azeotropic distillation facilitates removal of the water and is required for rapid and complete reaction. Other solid acid catalysts work for this reaction as well as water soluble acid catalysts such as concentrated sulfuric acid. The combination of acid catalyst and water removal leads to a very effective dehydration of the monoterpene THL. At a fairly large scale of 1 L, it was discovered that only 5 g of clay is required to afford complete conversion of THL to a mixture of 3,7-dimethyloctene isomers in a matter just a couple of hours. The benzene can be fully recovered and used indefinitely in the dehydration chemistry. Other azeotropic distillation aids such at toluene can be used in the process. Hydrogenation of the octene-isomers leads to near quantitative conversion of THL to 2,6-dimethyloctane (DMO). Ignition quality testing (IQT) of DMO afforded a derived Cetane Index for the fuel of 45, which compares very well with that predicted by theory.

Figure 1:
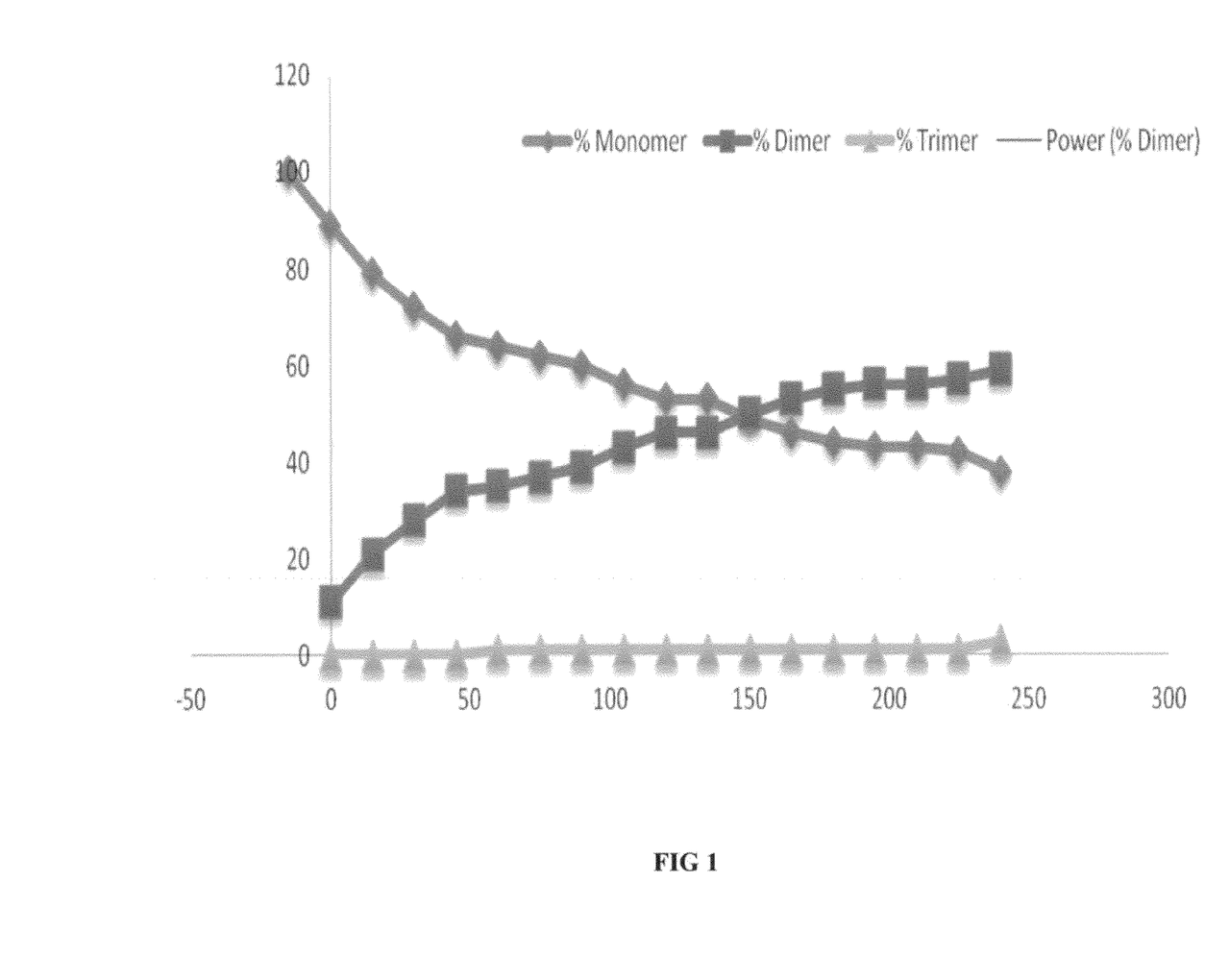
FIG. 1 is a graph plotting of monomer/dimer/trimer amounts as a function of reaction time over montmorillonite K10, according to embodiments of the invention.

When heating is continued after removal of the benzene, then the clay catalyst appears to quite effective at dimerization of the highly substituted 3,7-dimethyloctenes. Also observed was the formation of trimer ($C_{30}$-isomers) at extended reaction times, albeit this appears stay under ~5% when using the clay catalyst at modest loading levels. The resulting mixtures having monoterpene, $C_{20}$, and $C_{30}$ can be hydrogenated over palladium on carbon. At that point, when desired the DMO can be distilled away from the dimer/trimer mixture to afford a light yellow saturated hydrocarbon mixture of dimer and trimer. It was discovered that GC-MS data does in fact correspond quite well with the actually wt-% of DMO, dimers, and trimers obtained by distillation:

Running a dehydration/oligomerization reaction and pulling aliquots every 15 min followed by GC-MS analysis reveals a relatively gradual formation of dimer with minor amounts of trimer. The slowing down of dimer formation is likely due to a combination of catalyst deactivation and that the more reactive octene isomers (geometric and isomeric) are used up. FIG. 1 is a plot of monomer/dimer/trimer amounts as a function of reaction time over montmorillonite K10.

Figure 2:
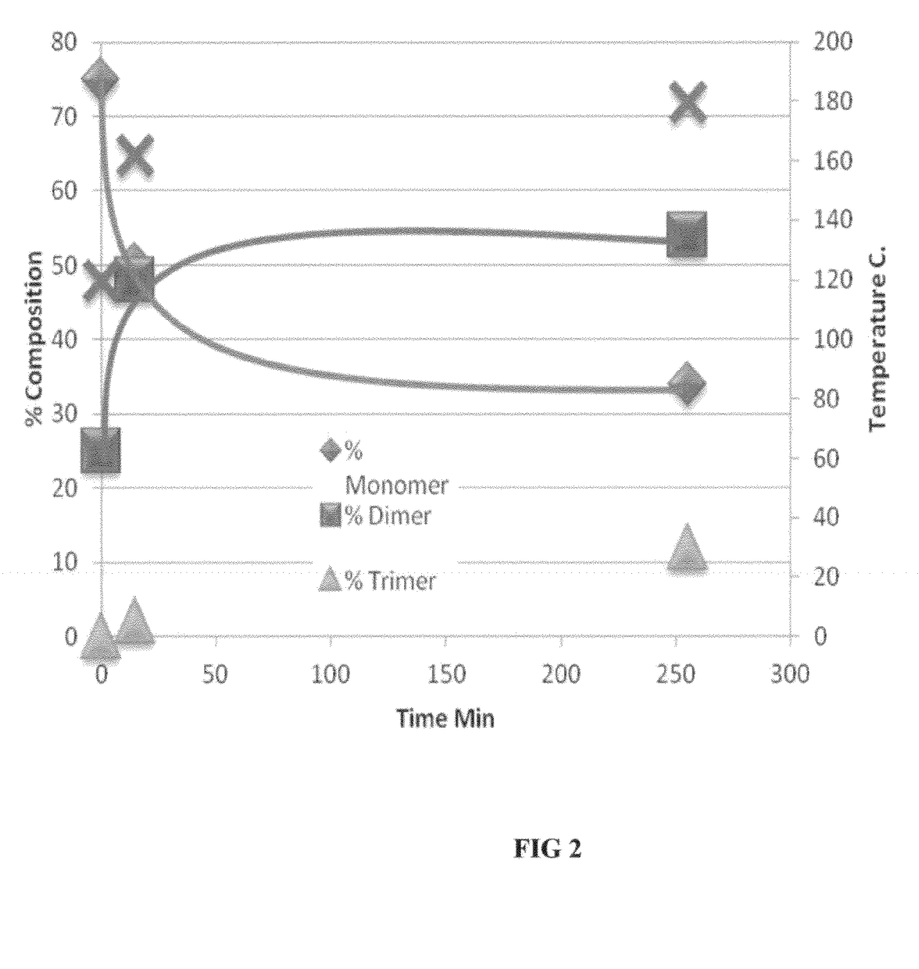
FIG. 2 is a graph showing data for a THL-dehydration-oligomerization run using 5 g of amberyst-15 and 100 mL of THL, according to embodiments of the invention.

Amberlyst-15 Dehydration/Oligomerization Chemistry. It was discovered that using modest loading of amberlyst-15 (8 g catalyst/500 mL THL) as catalyst leads to quantitative conversion of the THL to the mixture of octenes with indication of dimerization. As for the clay chemistry, when the benzene is removed from the reaction and the temperature is allowed to increase, this gives rapid formation of dimer, and then finally some trimer. Higher loadings of amberlyst-15 catalyst can lead to early formation of dimer as seen in the data plotted in FIG. 2. FIG. 2 is a graph showing data for a THL-dehydration-oligomerization run using 5 g of amberyst-15 and 100 mL of THL heated in a single vessel.

Figure 3:
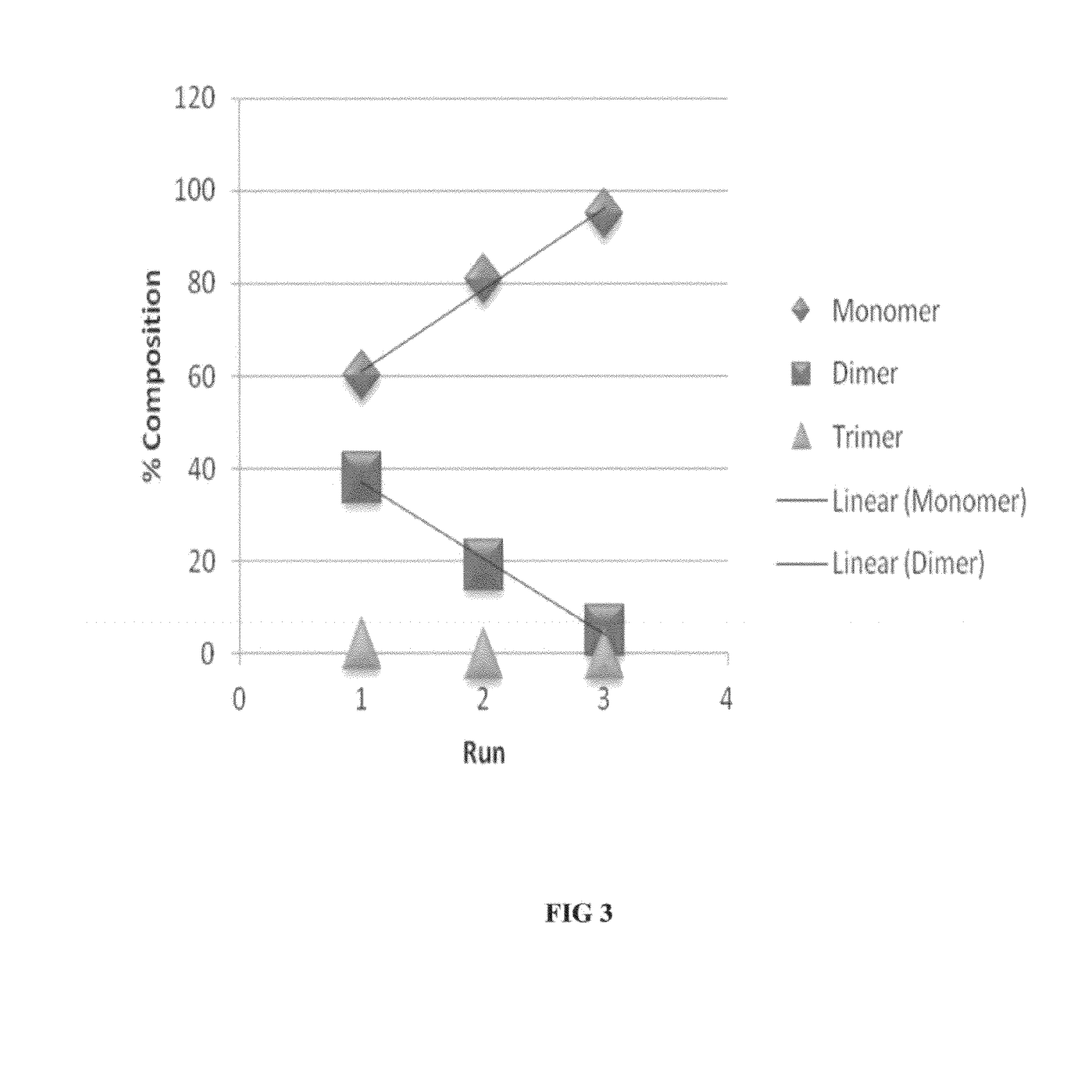
FIG. 3 is a graph showing data for the THL-dehydration-oligomerization reusing the same catalyst batch successively, according to embodiments of the invention.

Examined was the ability to recycle the amberlyst-15 catalyst with interesting results if one does not use the recycling system The data for a three-run sequence is displayed in FIG. 3. For each run at the point of water removal we find complete conversion of the THL to a mixture of dimethyl octene isomers. With continued heating and removal of the benzene, it was discovered that the used amberlyst-15 catalyst becomes less effective at dimerizing the octene isomers, clearly showing the advantages of the keeping the temperature low. The used Amberlyst-15 catalyst was treated with 10% sulfuric acid, washed, and then dried. The regenerated catalyst regained only a minor amount (<5%) of its original activity; thus, the porous structure of the catalyst has likely been destroyed in some fashion. FIG. 3 is a graph showing data for the THL-dehydration-oligomerization reusing the same catalyst batch successively. For each run data represents M/D/T ratio after removal of the benzene.

Figure 4:
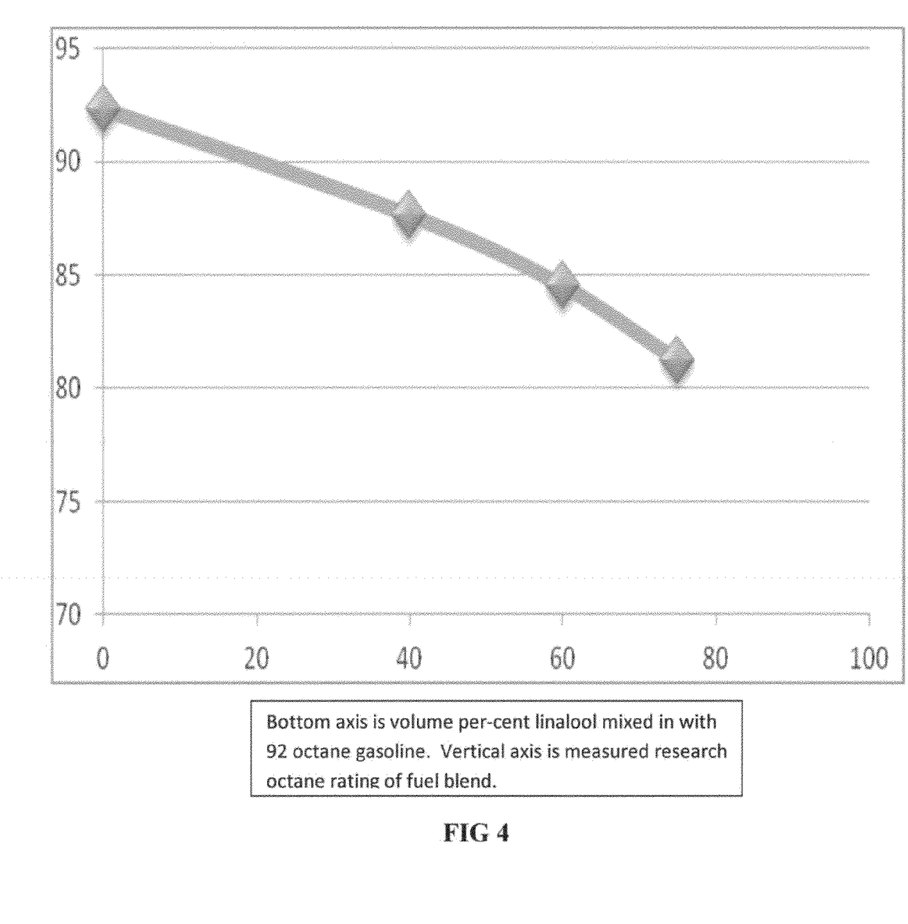
FIG. 4 is a graph plotting of research octane data for various mixtures of THL and standard gasoline based on volume percent (x axis is volume percent of THL in the mixture), according to embodiments of the invention.

The use of tetrahydrolinalool as an oxygenate-additive to gasoline is one embodiment of the invention. In FIG. 4 a plot of tetrahydrolinalool concentration (vol-%) as a function of research octane rating is plotted. What is quickly demonstrated is that the addition of 40 vol-% only leads to a minor reduction in octane rating yet provides a 40 vol-% bioblending component. In pure form the saturated terpene alcohol has a density of 0.83 g/mL and a calculated heat of combustion on a volume basis greater than gasoline. This 40%-vol blend meets the current oxygen requirement that limits ethanol blending to ~10 vol-%; thus, this instant result as an embodiment of this invention demonstrates that an expected and high level of tetrahydrolinalool can be used as a terpene-derived gasoline blending agent.

Figure 5:
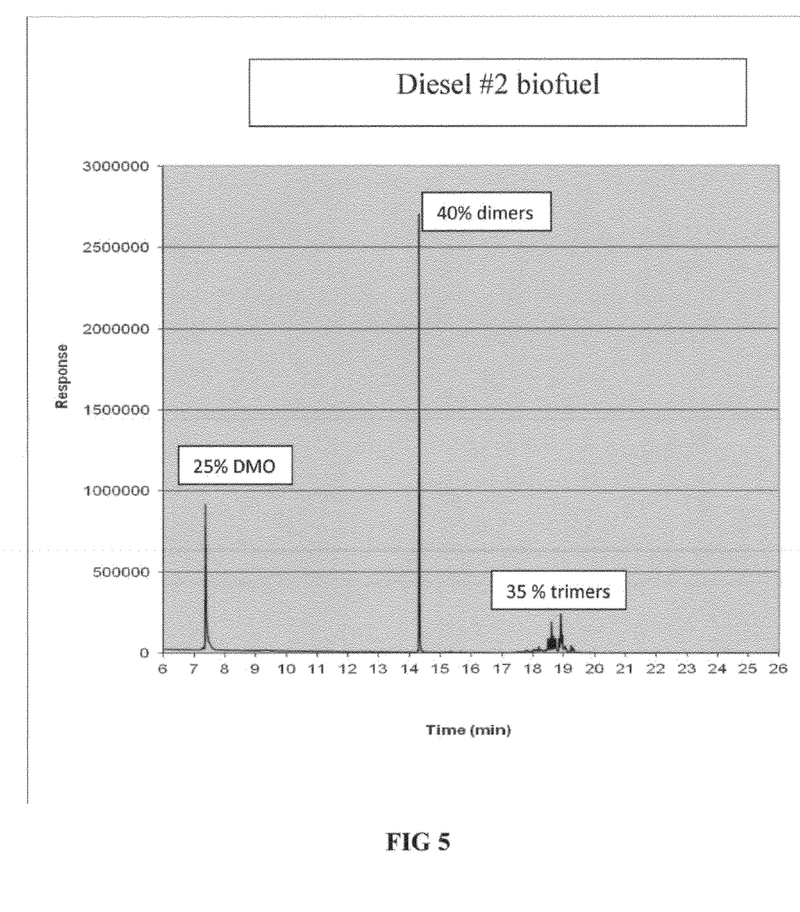
FIG. 5 is a GC-MS chromatogram verifying an example of blending 25% DMO, 40% dimers, and 35% trimers, as prepared in the embodiments of this invention. This is one example of a pure synthetic paraffinic kerosene meeting ASTM D975 diesel #2 requirements as an example of this instant invention.

In FIG. 5 is an example where components prepared as an embodiment of this can be blended to form pure synthetic paraffinic kerosene that can meet all diesel #2 requirements (ASTM D975). This fuel contains no aromatics, no sulfur, and can be tailored to by decreasing trimer content to have very specific viscosities and lubrication values, all within or exceeding ASTM D975 diesel fuel requirements. DMO can be used in ranges of 15 to 90 vol-%, with the dimers and trimers making up the remaining vol-% of the fuel. Specifically, trimers are useful for adding lubricity to the fuel at very low levels, for example <5 vol-%, significant changes in the HFRR wear tests can be seen (e.g. ~0.1 mm). Some data is summarized in Table 1 for a typical fuel blend.

TABLE 1

Testing Data for a fuel blend prepared as an embodiment of this invention.

| | | |
|---|---|---|
| Fp | ASTM D93 | >80° C. |
| Cetane (42 or greater) | IQT | 45 |
| Pour point (<-6° C. or better) | ASTM D97 | -20° C. |
| Zero acids | ASTM D974 | ~0 |
| Lubricity Diesel #2 spec | HFRR | <0.5 |
| Density (0.876 max) | lab | 0.79 g/mL |
| Corrosion (No. 1) | ASTM D130 | 1a |
| Elemental Anal. | Atlantic Micro lab | C 85.5; H 14.5 |
| >43 MJ/Kg energy | D4529 | 44.0 |
| Demulsification (10 max) | D1401 | 5 |

Figure 6:
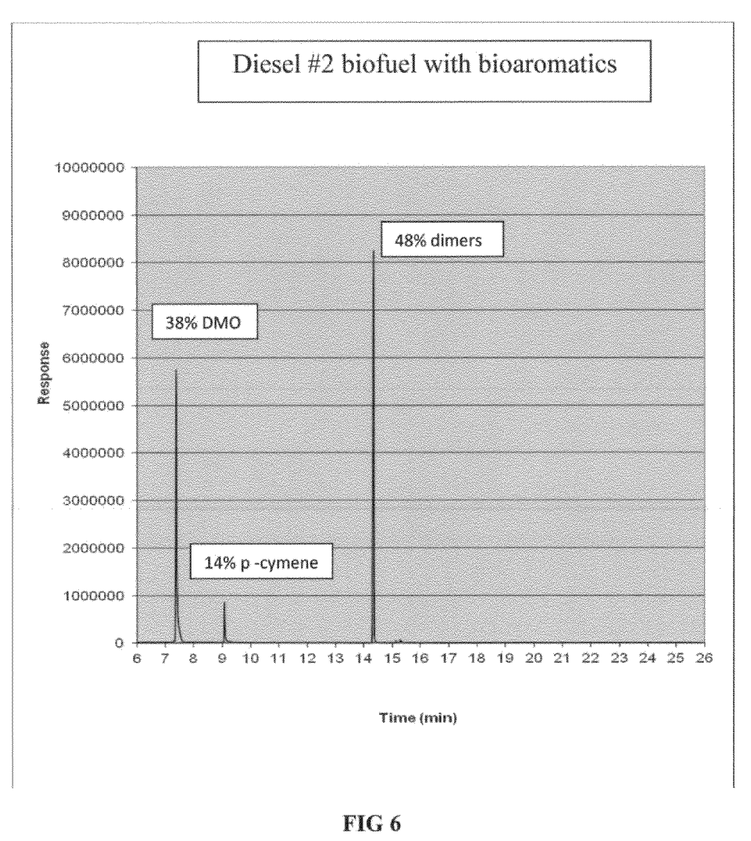
FIG. 6 is a GC-MS chromatogram verifying an example of blending 38% DMO, 14% p-cymene, and 48% dimers, as prepared in the embodiments of this invention. This is one example of a pure synthetic paraffinic kerosene meeting ASTM D975 diesel #2 requirements containing aromatics as an example of this instant invention.

In FIG. 6 is an example of where a bioaromatic has been added to a Diesel #2 surrogate biofuel using the some embodiments of the invention. The bioaromatic is p-cymene. The latter is prepared from linalool using selected catalytic chemistries (1981, Wideman and Kuczkowski in U.S. Pat. No. 4,382,152). Thus, in this invention it is demonstrated that surrogate biodiesels containing aromatics can be formulated based on starting from a single monoterpene alchohol.

Figure 7:
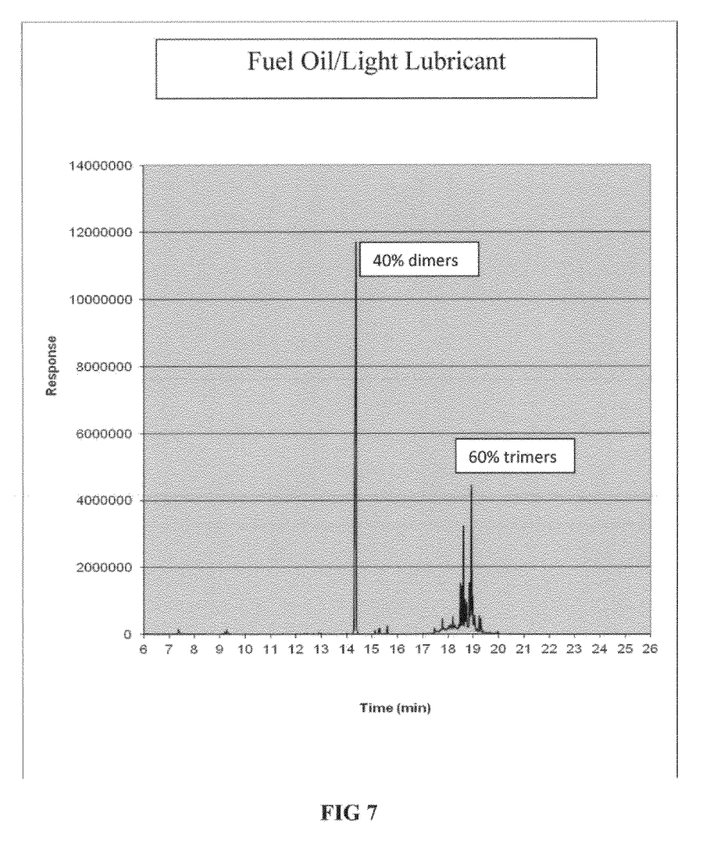
FIG. 7 is a GC-MS chromatogram verifying an example of blending 40% dimers and 60% trimers, as prepared in the embodiments of this invention. This is one example of a pure synthetic paraffinic kerosene useful as fuel oil or light lubricant as a bioproduct of this instant invention.
Figure 8:
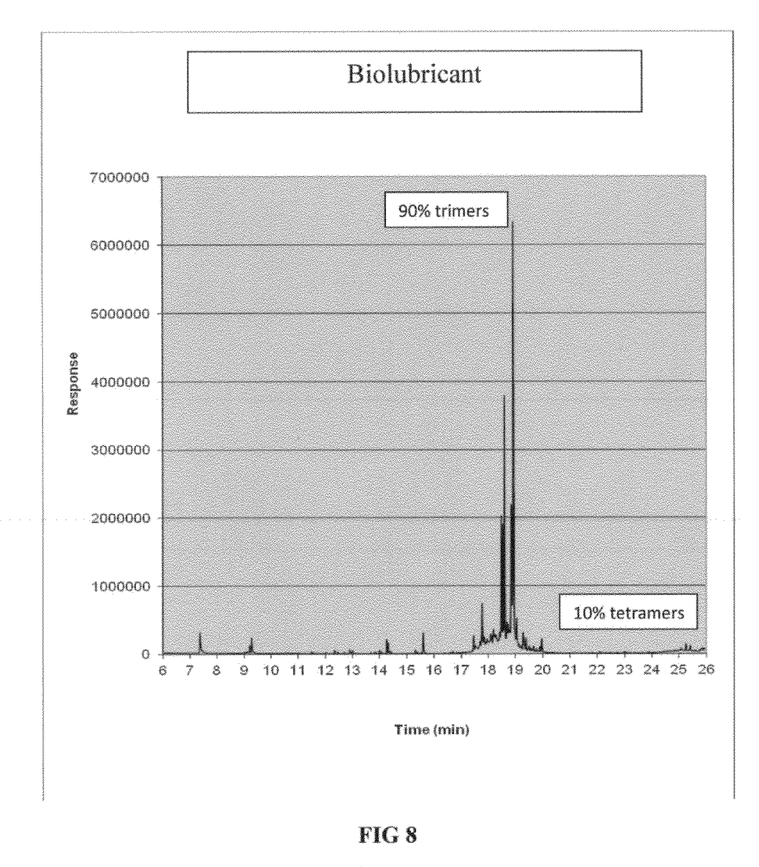
FIG. 8 is a GC-MS chromatogram verifying an example of blending 90% trimers and 10% tetramers as prepared in the embodiments of this invention. This is one example of a pure synthetic paraffinic kerosene useful as a biolubricant as an example of this instant invention.

In FIG. 7 a heavy fuel blend is made that can be used as fuel oil or a light lubricant. This heavy fuel is a pure synthetic paraffinic kerosene and as all embodiments of the invention the kerosene component is 100% iso-paraffinic; hence, each embodiment of this invention has freezing points much lower (>20° C.) when compared to any fatty acid methyl ester (FAME) biodiesel fuel. This is a direct result that fuels and lubricants created in this invention are 100% iso-paraffinic and this is well known by those experienced in the art of fuels to afford superior freezing point performance (i.e. a decrease in freezing point). In FIG. 8 a GC-MS chromatogram is presented showing the composition of a biolubricant prepared from embodiments of this invention. The biolubricant is prepared by blending 90% of the trimers with 10% of the tetramers obtained through extensive heating with catalysts described as embodiments of the invention. This type of biolubricant is a 100% synthetic paraffinic kerosene having 100% of an iso-paraffinic chemical structure. This leads to very low freezing points of biolubricants prepared an embodiment of the invention.

Experimental Procedures Used.

General Methods. All manipulations of compounds and solvents were carried out using standard Schlenk techniques. $^1$H and $^{13}$C NMR measurements were performed using either a Bruker 300 or Bruker 400 MHz NMR instrument. $^1$H and $^{13}$C NMR chemical shifts are reported versus the deuterated solvent peak (Solvent: $^1$H, $^{13}$C: CDCl$_3$, δ 7.25 ppm, δ 77.0 ppm). Anhydrous THF, inhibitor free anhydrous diethyl ether, tetrahydrolinalool, linalool, Amberlyst-15, 10% palladium on carbon, and platinum oxide (PtO$_2$) were purchased from Aldrich Chemical Co. and used as received. Elemental analyses were performed at Atlantic Microlab, Inc., Norcross, Ga.

Attempted Hydrogenation of Geraniol: A PARR 1.5 L low pressure glass hydrogenation vessel (150 psig) was charged with 500 mL of geraniol and 10 g of palladium on carbon. The vessel was pressurized to 60 psig, evacuated, and back filled with hydrogen three times. The mixture was allowed to react with stirring at 40° C. under 60 psig of hydrogen for 72 h. Venting, filtration, and then NMR spectroscopic analysis of the reaction mixture indicated it was all geraniol, consistent with no hydrogenation taking place.

Hydrogenation of Linalool to Tetrahydrolinalool; A PARR 1.5 L low pressure glass hydrogenation vessel (150 psig) was charged with 500 mL of linalool and 10 g of palladium on carbon. The vessel was pressurized to 60 psig, evacuated, and back filled with hydrogen three times. The mixture was allowed to react with stirring at 40° C. under 60 psig of hydrogen for 72 h. Venting, filtration, and then NMR spectroscopic analysis of the reaction mixture indicated it was tetrahydrolinalool (99%+purity by GC-MS).

Single-pot/Single-catalyst Sequential Dehydration/Oligomerization of Tetrahydrolinalool:Montmorillonite K10: A three neck flask fitted with a dean-stark trap and reflux condenser, thermometer port, and stopper was charged with tetrahydrolinalool (413 g, 500 mL), montmorillonite K 10 catalyst (4.0 g), benzene (50 mL), and a stir bar. The flask was heated using a heating mantle connected to a variac and the flask was covered for insulation. With stirring, the mixture was heated to reflux. After 70 min the pot temperature reached 103° C. and the benzene began delivering water into the dean-stark trap by azeotropic removal. The water then separated and was drained as formed. The azeotropic removal of water covered a period of ~85 min. An aliquot was removed and the reaction continued. After no more water was formed, the vessel temperature reached 141° C. and all the benzene condensed in the Dean-Stark trap was drained and used for subsequent reactions. A near quantitative recovery of the benzene was achieved in ~25 min. After removal of the benzene, the vessel temperature attained a temperature of 151° C. Continued heating of the reaction mixture led to the pot temperature reaching 162° C. and then slowly climbed up to a maximum temperature of 177° C. over a period of 1 h. The mixture was then held that temperature of 177° C. for the duration of the reaction.

Single-Pot/Single-Catalyst Sequential Dehydration/Oligomerization of Tetrahydrolinalool; Amberlyst-15:

A three neck flask fitted with a dean-stark trap and reflux condenser, thermometer port, and stopper was charged with tetrahydrolinalool (~400 g, ~490 mL), Amberlyst-15 (10 g), benzene (50 mL), and a stir bar. The flask was heated using a heating mantle connected to a variac and the flask was covered for insulation. With stirring, the mixture was heated to reflux. After 70 min the pot temperature reached 101° C. and the benzene began delivering water into the dean-stark trap by azeotropic removal. The water then separated and was drained as formed. The azeotropic removal of water covered a period of ~90 min. An aliquot was removed and the reaction continued. After no more water was formed, the vessel temperature was 141° C. formed the benzene was condensed and removed in the Dean-Stark trap. The vessel temperature reached during 135° C. for this process. A near quantitative recovery of the benzene was achieved in ~30 min. After removal of the benzene the vessel temperature attained a temperature of ~150° C. After benzene removal, the reaction was continued benzene removal the pot temperature hit ~160° C. and slowly climbed up to a maximum temperature of 180° C. within 1 h and then held at that temperature for the duration of the reaction.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

It is to be understood that the foregoing is exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A fuel produced by the methods, comprising:
hydrogenating at least one acyclic monoterpene alcohol with at least one transition metal hydrogenation catalyst to produce a fully saturated monoterpene alcohol tetrahydrolinalool (THL);
dehydrating said tetrahydrolinalool (THL) with at least one acid catalyst and azeotropic distillation and recovering benzene to produce 3,7-dimethyloctene isomers;
acid catalyzing reaction of said 3,7-dimethyloctene isomers and recovering benzene;
hydrogenating said 3,7-dimethyloctene isomers with at least one transition metal catalyst to produce a mixture of 2,6-dimethyloctane (DMO), dimers ($C_{20}$ isomers), and trimers ($C_{30}$ isomers);
distillation isolating said 2,6-dimethyloctane (DMO), dimers ($C_{20}$ isomers), and trimers ($C_{30}$ isomers) from said mixture to produce a substantially purified set of $C_{10}$ to $C_{30}$ for producing fuels; and
leaving said distillation pot residue ($C_{40}+$) for subsequent use biolubricant additives.

2. The fuel according to claim 1, further comprising recombining portions of DMO, C-20 dimer, and C-30 trimer that meet ASTM D975 specifications for Diesel #2.

3. A fuel produced by the methods, comprising:
hydrogenating at least one acyclic monoterpene alcohol (linalool) with at least one catalyst comprised of a late transition metal to produce tetrahydrolinalool (THL);
dehydrating said tetrahydrolinalool (THL) with at least one acid catalyst and azeotropic distillation and recovering benzene to produce 3,7-dimethyloctene isomers; and
hydrogenating said 3,7-dimethyloctene isomers with at least one late transition metal catalyst to produce 2,6-dimethyloctane (DMO), dimers ($C_{20}$ isomers), and trimers ($C_{30}$ isomers).

4. A fuel blend produced by combining said 2,6-dimethyloctane (DMO) produced by the methods of hydrogenating at least one acyclic monoterpene alcohol with at least one transition metal hydrogenation catalyst to produce a fully saturated monoterpene alcohol tetrahydrolinalool (THL); dehydrating said tetrahydrolinalool (THL) with at least one acid catalyst and azeotropic distillation and recovering benzene to produce 3,7-dimethyloctene isomers; acid catalyzing reaction of said 3,7-dimethyloctene isomers and recovering benzene; hydrogenating said 3,7-dimethyloctene isomers with at least one transition metal catalyst to produce a mixture of 2,6-dimethyloctane (DMO), dimers ($C_{20}$ isomers), and trimers ($C_{30}$ isomers); distillation isolating said 2,6-dimethyloctane (DMO), dimers ($C_{20}$ isomers), and trimers ($C_{20}$ isomers) from said mixture to produce a substantially purified set of $C_{10}$ to $C_{30}$ for produce said fuels blend; and leaving said distillation pot residue ($C_{40}+$) for subsequent use biolubricant additives; and said dimers ($C_{20}$ isomers) produced by the methods of hydrogenating at least one acyclic monoterpene alcohol (linalool) with at least one catalyst comprised of a late transition metal to produce tetrahydrolinalool (THL); dehydrating said tetrahydrolinalool (THL) with at least one acid catalyst and azeotropic distillation and recovering benzene to produce 3,7-dimethyloctene isomers; and hydrogenating said 3,7-dimethyloctene isomers with at least one late transition metal catalyst to produce 2,6-dimethyloctane (DMO).

5. A fuel blend produced by the methods, comprising:
hydrogenating at least one acyclic monoterpene alcohol with at least one transition metal hydrogenation catalyst to produce a fully saturated monoterpene alcohol tetrahydrolinalool (THL);
dehydrating said tetrahydrolinalool (THL) with at least one acid catalyst and azeotropic distillation and recovering benzene to produce 3,7-dimethyloctene isomers;
acid catalyzing reaction of said 3,7-dimethyloctene isomers and recovering benzene;
hydrogenating said 3,7-dimethyloctene isomers with at least one transition metal catalyst to produce a mixture of 2,6-dimethyloctane (DMO), dimers ($C_{20}$ isomers), and trimers ($C_{30}$ isomers);

distillation isolating said 2,6-dimethyloctane (DMO), dimers ($C_{20}$ isomers), and trimers ($C_{20}$ isomers) from said mixture to produce a substantially purified set of $C_{10}$ to $C_{30}$ for producing said fuel blends; and leaving said distillation pot residue ($C_{40}+$) for subsequent use biolubricant additives.

6. The fuel blend according to claim 5, further comprising combining a mixture of $C_{20}$ dimer, $C_{30}$ trimer, and said pot residue ($C_{40}+$).

7. The fuel blend according to claim 5, further comprising combining said 2,6-dimethyloctane (DMO), a fully saturated $C_{15}$ sesquiterpene (farnesane), and said dimers ($C_{20}$ isomers) that meets ASTM specifications D975.

* * * * *